United States Patent [19]

Rebman

[11] Patent Number: 4,521,685
[45] Date of Patent: Jun. 4, 1985

[54] TACTILE SENSOR FOR AN INDUSTRIAL ROBOT OR THE LIKE

[75] Inventor: Jack Rebman, Cary, N.C.

[73] Assignee: Lord Corporation, Erie, Pa.

[21] Appl. No.: 353,435

[22] Filed: Mar. 1, 1982

[51] Int. Cl.$^3$ .............................................. G01D 5/34
[52] U.S. Cl. .................................... 250/229; 901/33; 414/5
[58] Field of Search ......................... 340/365 L, 365 P; 250/221, 211 K, 229, 231 P, 231 R; 73/862.64, 862.04; 901/33; 414/5, 6, 730, 735

[56] References Cited

U.S. PATENT DOCUMENTS

| | | | |
|---|---|---|---|
| 3,263,498 | 8/1966 | Hagman et al. | 73/862.64 |
| 3,580,157 | 5/1971 | Casebeer | 250/229 |
| 3,909,234 | 9/1975 | Hill et al. | 250/229 |
| 4,092,532 | 5/1978 | Hayes | 250/229 |
| 4,283,714 | 8/1981 | Trenkler et al. | 340/365 L |
| 4,405,197 | 9/1983 | Bejczy | 350/96.15 |

OTHER PUBLICATIONS

Collins et al., Hall Effect in Magnetic Core Keyboard Jun. 1970, IBM Tech. Disclosure, vol. 13, No. 1, p. 189.

Primary Examiner—David C. Nelms
Assistant Examiner—J. Brophy
Attorney, Agent, or Firm—Joseph H. Heard

[57] ABSTRACT

A tactile sensing system is provided which consists of essentially four components including a touch surface having a plurality of mechanically and electrically isolated sensitive sites, transducer means associated with each of the sensitive sites for converting a mechanical response to an electrical signal, first signal processing means for scanning the signals produced by the transducer means and converting such signals to digital format, and second signal processing means including a computer for interpreting and displaying the data. The system of this invention is capable of providing high contrast, high normal load resolution, moderate spatial resolution and high sensitivity to determine such mechanical contact parameters as presence, pressure, pressure pattern, texture, hardness and topography of an object contacting the touch surface. In addition, separate means are included enabling the system to detect the location, magnitude and direction of shear forces applied to the touch surface.

21 Claims, 19 Drawing Figures

TACTILE SENSOR FOR AN INDUSTRIAL ROBOT OR THE LIKE

FIELD OF THE INVENTION

This invention relates to the field of tactile sensing, and, more particularly, to a device capable of detecting, discriminating and recognizing a number of mechanical contact phenomena including presence, pressure, pressure pattern, incipient slip, slip, texture, hardness, and topography.

BACKGROUND OF THE INVENTION

Many areas have been identified where it is desirable to have an artificial sense of touch. The most commonly mentioned applications include the field of automation, particularly industrial robotry, tele-operation as employed in remote manipulation underwater, in spacecraft, or with extraterrestrial landing vehicles, and also in the field of prosthetic devices for amputees or those handicapped with loss of nerve function. In all of these applications, information about an object being contacted or manipulated is necessary to make a characterization of the object such as size, shape, weight, orientation and other contact aspects, and then based on such characterization computer-controlled decisions can be made such as properly grasping, moving, manipulating, placing and releasing the object.

Considering the area of industrial robotry, which appears to be a particularly good candidate for devices having tactile sensing capability, it is estimated that approximately 75% of the manufacturing conducted in the United States is low volume or batch operations performed by manual labor and accounting for approximately 30% of the gross national product. Machine replacement of human labor in at least a portion of such activities can result in improved accuracy, quality, speed, safety, efficiency and economy. It has been estimated that the cost of human labor in only the last decade has increased at a rate of more than five times the cost of robotic labor. In addition, this estimate does not take into consideration that robots can operate machine tools, for example, with a repeatable precision that may take a human worker many years to acquire. Manufacturing operations which potentially could be accomplished by devices having tactile sensing capabilities include assembly, fast adaptive grasping or the pick-up of randomly oriented parts from assembly lines, bin picking, grinding, deburring, polishing and welding among others.

Tactile sensing systems have been introduced in recent years but generally have met with little success and are of limited practical utility. For example, typical prior art tactile sensing systems are shown in U.S. Pat. No. 4,014,217 to Lagasse et al, and U.S. patent application Ser. No. 6-225,500 to Raibert et al entitled "Tactile Sensing System" and available from NTIS. The tactile pick-up system of Lagasse et al includes a continuous outer layer of material which has a variable electrical conductivity as a function of its state of compression. A matrix of measuring electrodes mounted to the layer of variable electric conductivity are operable to measure the electric field produced by compression of the layer in response to contact with an object. In this design, the continuous outer layer itself is electrically responsive to force exerted by contact with an object. When compressed, the electrical conductivity of the layer is altered at the adjacent to the point of contact and this changed condition is detected by the electrodes.

One problem of the Lagasse et al design is low contrast caused by the continuous nature of the pressure-sensing electrically conductive outer layer. While placement of an object on the outer layer will cause it to deflect and thus change the electrical conductivity of the layer immediately beneath the object, such deflection cannot be confined or isolated to the limited area of the object's dimensions. This is true because portions of the outer layer immediately adjacent those portions contacting the object must also be deflected or compressed at least to some degree by the object. The compression of adjoining or contiguous portions of the layer causes a current to be conducted there which is sensed by the electrodes. Therefore, instead of sensing current only at those locations along the outer layer where an object actually makes contact, prior art devices such as Lagasse et al tend to produce false or incorrect signals from adjacent areas resulting in relatively low resolution or inaccurate characterization of an object's presence, pressure, size, shape and similar contact parameters. To the extent that such false signals or "cross-talk" may be circumvented in Lagasse et al, complex pattern recognition systems would be required.

For purposes of discussing the prior art and also the structure and advantages of this invention, the term contrast will be used in reference to the extent which a tactile sensing system is capable of sensing the boundaries of an object contacting the sensitive surface of the device. The term resolution will refer to the minimum change in load that can be detected, both in terms of the magnitude and location of such load on the sensing surface. Therefore, in describing a tactile sensing system having high or low contrast, for example, such terms may be considered as an indication of the system's ability or inability to accurately characterize the boundaries of an object contacting the sensing surface of the device.

In the Raibert et al patent application, a tactile sensing system is disclosed which is similar to the Lagasse et al system in that a layer or sheet of material is disposed over an array or matrix of measuring electrodes which are operable to produce a signal in response to contact of an object with the surface of the layer. A sheet of pressure sensitive conductive plastic forms the layer in Raibert and the resistivity of the sheet changes in a known manner as a function of its deformation. The array or matrix of measuring electrodes senses such change in resistivity and relays that information to electrical components for processing. For the same reasons as discussed in connection with the Lagasse et al patent, this approach suffers from a limited resolution capability since it is difficult to localize or isolate the strain imposed by contact with an object to be sensed to a limited area where a continuous sensing surface is utilized.

Additionally, a common limitation of the overlayer material used in the above cited prior art is that such material is not rugged in construction and may be susceptible to failure particularly in the harsh environment found in many manufacturing operations. A cut, abrasion or other surface irregularity could easily alter the conductive or resistive properties of the outer layers in Lagasse et al and Raibert respectively. Since the sensing capability of each system is dependent on the integrity of the outer layer, which layer accomplishes the actual sensing function, it is axiomatic that change to the layer would render the entire system inoperable. Moreover, electrically conductive or resistive elastomers or other polymers generally exhibit poor hysterisis, excessive set and poor mechanical strength. All of these physical properties make such materials undesirable for use in many tactile sensing applications.

It has therefore been an object of this invention to provide a tactile sensing system which is capable of high contrast sensing of the magnitude and location of the deflection caused by contact of an object to be manipulated with the sensing surface of the system.

It is another object herein to provide a tactile sensing system capable of sensing parameters when contacting an object such as presence, pressure, size, shape, location and orientation among others.

It is a further object to provide a tactile sensing system having the dual capability of sensing shear and normal loads imposed by contact with an object.

Another object herein is to provide a tactile sensing system having the combination of high contrast normal force detecting capability and separate moderate resolution shear force detecting capability.

It is still another object to provide a tactile sensing system having a touch surface with individual sensing means for contacting an object which are separate from one another and exhibit little or no deflection when adjacent sensing means contact an object.

It is a still further object herein to provide a touch surface of rugged construction which acts to transfer load in the form of mechanical movement for measurement by sensing means.

It is another object of the invention to provide a sensing system having a touch surface with sensitive sites whose compliance may be controlled through material choice and/or geometrical configuration for varying the response of such sites to deflection by contact with an object.

SUMMARY OF THE INVENTION

These objectives are accomplished in this invention of a tactile sensing system having essentially four components including a touch surface with a plurality of sensitive sites, transducer means associated with each of the sensitive sites for converting a mechanical response to an electrical signal, localized data processing means, and finally remote signal processing means including a control computer, buffer and display. In one embodiment of the invention, this combination of components is operable to sense the deflection of the touch surface in response to normal forces induced by an object contacting the touch surface, and to analyze the magnitude and location of such deflection to determine such contact parameters as presence, pressure, pressure pattern, texture, hardness and topography of the object.

As discussed in detail below, an object placed on or against the touch surface of the tactile sensing system herein contacts a number of sensitive sites depending on the object's size, and causes such sensitive sites to deflect. The extent of this deflection or mechanical response is sensed by individual transducer means associated with each of the sensitive sites, and an analog signal is produced by each transducer means. The analog signals are placed in digital format by circuitry located adjacent the transducer in a manner described below. The digital signals are then sent to external signal processing means including a computer where they are interpreted and expressed on a visual display or other means to indicate various mechanical contact parameters of the object as mentioned above.

In a further embodiment of this invention, shear detection transducer means may be added to the tactile sensing system to detect with at least moderate contrast, the magnitude, location and direction of the shear force applied to the touch surface by an object. This provides the tactile sensing system herein with the additional capabilities needed to detect slip and incipient slip of an object contacting the touch surface.

DESCRIPTION OF THE DRAWINGS

The structure, operation and advantages of this invention will become apparent upon consideration of the following discussion taken in conjunction with the accompanying drawings, wherein.

DESCRIPTION OF THE INVENTION

Figure 1:
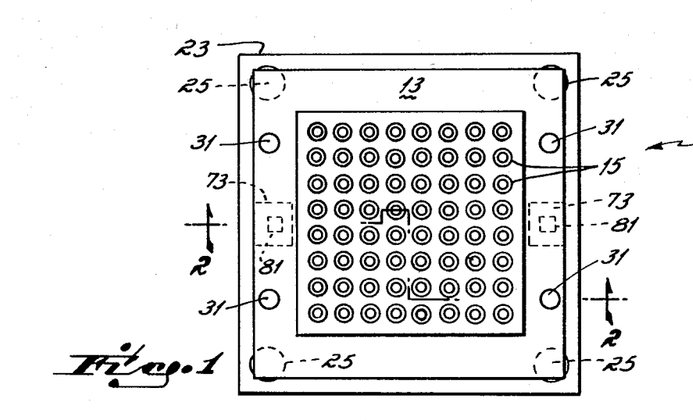
FIG. 1 is a plan view of the tactile sensing system of the invention showing the touch surface and array of sensitive sites.
Figure 2:
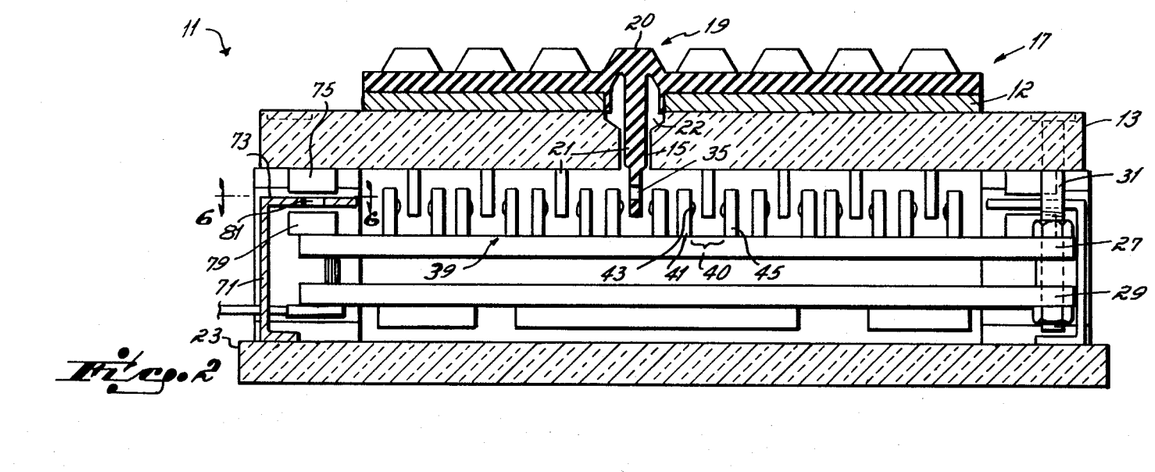
FIG. 2 is a partial cross-sectional view in full elevation of the tactile sensing system taken generally along line 2—2 of FIG. 1.

Referring now to the drawings and in particular to FIGS. 1 and 2, the tactile sensing system of this invention is labelled generally with the reference numeral 11. As mentioned above, the system 11 consists of essentially four components including a touch surface having an array of sensitive sites, transducer means for detecting normal load, local signal processing means and remote signal processing means. Additionally, the system 11 may include separate shear detection transducer means for providing the capability needed to detect such contact parameters as slip and incipient slip.

Specifically, system 11 includes a top plate 12 and a support plate 13 which are secured together and formed with sixty-four chamfered openings 15 disposed in a matrix configuration of eight rows and eight columns. It should be understood that while an 8×8 array is shown in FIG. 1, other matrices could be utilized depending on the space and size requirements of a particular application. A touch surface is provided, labeled generally with the reference 17, and it includes sensitive sites 19 disposed in a matrix configuration corresponding to that of the openings 15 in plates 12 and 13. The touch surface 17 is a unitary element formed of resilient material such as elastomer or a suitable functional equivalent, which is rugged in construction and capable of withstanding harsh environments without appreciable damage or deterioration.

Each of the sensitive sites 19 includes a raised section 20 of resilient material which extends upwardly from the remainder of the touch surface 17. Integrally connected to each of the raised sections 20 is a pin structure 21 which extends downwardly through the openings 15 in support plates 12 and 13. The diameter of the pin structure 21 is less than that of the raised section 20 forming an annular hollow section 22 between the pin structure 21 and the adjacent opening in support plate 13. Once in place with all of the pin structures 21 in openings 15, the touch surface 17 is secured to top plate 12 by adhesives or any other suitable means.

Each of the sensitive sites 19 is resilient so that they undergo a vertical deflection in response to the application of a normal force to the raised section 20, as would occur for example when an object is placed on the touch surface 17. Each of the sensitive sites 19 which the object contacts are deflected downwardly, which, in turn, causes the pin structure 21 of those affected sensitive sites 19 to move downwardly. For purposes of the present discussion, this deflection will be called the mechanical response to the application of a normal force to the touch surface 17. The remainder of the components of system 11 include means of sensing this mechanical response, producing electrical signals as a measure of the existence, location and magnitude of the response, and then processing such signals so that contact parameters of the object causing the mechanical response can be interpreted and identified.

A base section 23 is disposed beneath plate 13 and is connected thereto by compliant mounts 25 attached at each of the four corners of the base 23 and plate 13. The mounts 25 are moderately compliant in shear and relatively stiff in compression, thus permitting motion of the plate 13 relative to the base section 23 along a horizontal plane parallel to the plane of the plate 13, but very little motion of the plate 13 vertically with respect to base section 23. A transducer platform 27 disposed beneath the plate 13, and an electronics platform 29 disposed between the transducer platform 27 and base 23, are connected together and to the plate 13 by means of bolts 31 or other suitable structural supports. Therefore, the platforms 27 and 29 are movable with the plate 13 as a unit relative to the fixed base section 23.

As mentioned above, an object placed on a sensitive site 19 will cause the pin structure 21 to deflect vertically downwardly. The magnitude of such deflection or mechanical response is directly proportional to the weight of the object or the magnitude of the normal force applied. This mechanical response is measured by a plurality of transducers mounted to the transducer platform 27 in an array or matrix corresponding to that of the sensitive sites 19 so that each pin structure 21 is provided with an individual transducer.

Figures 3, 3A, 4, 4A, 5, 5A, 6, 6A, 6B:
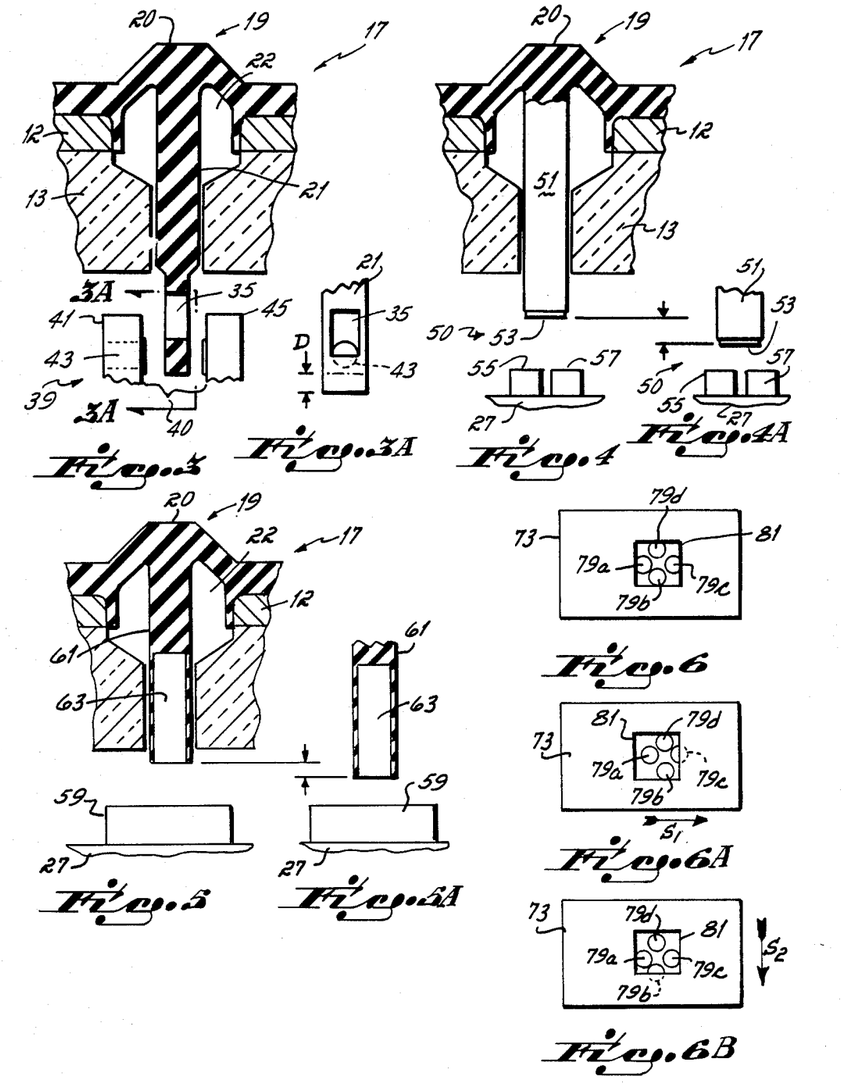
FIG. 3 is an enlarged partial cross-sectional view of one embodiment of the transducer means herein associated with a sensitive site in an undeflected position.
FIG. 3a is a partial view of the transducer means of FIG. 3 with the sensitive site in a deflected position.
FIG. 4 is a partial cross-sectional view of an alternate embodiment of the transducer means herein with the sensitive site in an undeflected position.
FIG. 4a is a partial view of the transducer means of FIG. 4 with the sensitive site in a deflected position.
FIG. 5 is a partial cross-sectional view of a still further embodiment of the transducer means with the sensitive site being in an undeflected position.
FIG. 5a is a partial view of the transducer means of FIG. 5 with the sensitive site in a deflected position.
FIG. 6 is a view in partial cross-section taken generally along line 6—6 in FIG. 2 of one embodiment of the shear detection transducer means herein, with the touch surface being in a normal position.
FIG. 6a is a view of the shear detection transducer means of FIG. 6 with a shear force $S_1$ acting on the touch surface.
FIG. 6b is another view of the FIG. 6 shear detection transducer means with a shear force $S_2$, perpendicular to $S_1$, acting on the touch surface.

In the embodiment of the invention shown in FIGS. 1–3, the pin structure 21 is essentially continuous, except for an opening or window 35 formed at a discrete location along the length thereof. The transducers of this embodiment, labeled generally with the reference 39, consist of a photo emitter 41 operable to produce a beam of light through a lens aperture 43 and a photo detector 45 which is capable of detecting the amount of intensity of light produced by the emitter 41. The detector 45 and emitter 43 are mounted to the transducer platform 27 such that the pin structure 21 extends in the gap 40 formed therebetween. In an undeflected, unloaded position as shown in FIG. 3, the lowermost portion of pin structure 21 blocks the passage of light between the emitter 41 and detector 43. However, as the pin structure 21 moves downwardly in response to contact of an object placed on the touch surface 17, the window 35 in pin structure 21 moves in the path of the light beam produced by emitter 41 allowing an amount of light directly proportional to the magnitude of the deflection D, for example, to be detected by detector 43. See FIG. 3a. In turn, the detector 43 produces a signal which is directly proportional to the intensity of light it senses, which signal is sent to the local electronic circuitry for processing as discussed below. This method of detecting the mechanical response of the touch surface 17 may be termed interrupted light transduction.

A second type of transduction means is shown in FIGS. 4 and 4a in which a transducer 50 is shown in combination with a modified pin structure 51. In this embodiment, the bottom of pin structure 51 is formed with a reflective surface 53. Mounted side-by-side on the transducer platform 27 directly beneath the mirror 53 of pin structure 51 are a photo-emitter 55 and photo-detector 57. The emitter 55 is operable to produce a light beam, and the detector 57 produces a signal directly proportional to the intensity of light which it senses.

In an undeflected position, as shown in FIG. 4, the mirror 53 is disposed a relatively large distance away from the emitter 55 so that a nominal amount of light is reflected by the mirror 53 and detected by the detector 57. Downward motion of the pin structure 21 in response to contact of an object placed on the touch surface 17, as shown in FIG. 4a, causes the intensity of light reflected back by the mirror 53 to the detector 57 to be increased in direct proportion to the proximity of the mirror 53. This method of transduction may be termed, for purposes of this discussion, reflected light transduction.

A third embodiment of the transduction means for sensing the mechanical response of the touch surface 17 to contact of an object placed thereon is shown in FIGS. 5 and 5a. A plurality of Hall effect transducers 59 are mounted to the transducer platform 27 immediately beneath each of the sensitive sites 19. Each of the sensitive sites 19 are formed with a pin structure 61 having a magnet 63 attached or embedded in its lower end adjacent the Hall effect transducers 59. As noted above, the pin structure 61 moves downwardly in response to a normal force applied by an object placed on the touch surface 17. The Hall effect transducer 59 is operable to sense the intensity of the magnetic field produced by the magnet 63 embedded in the pin structure 61 in an undeflected or deflected position as shown in FIGS. 5 and 5a. The intensity of the magnetic field detected by the Hall effect transducer 59 is directly proportional to the proximity of the magnet 63, and, in turn, the magnitude of the normal force applied to the touch surface 17 which controls the relative position of the magnet 63.

The transducers described above function to sense the mechanical response of the touch surface 17 to a normal load applied thereto due to contact with an object. As discussed below, signals produced by the transducers are processed in both local and remote electronic circuitry to produce a visual display or written indicia of so-called mechanical contact phenomena or parameters for an object. Such contact parameters include presence, pressure, texture, hardness and topography or shape among others. If the system 11 was adapted with the hand or grasping portion of an arm in an industrial robot, for example, the mechanical contact parameters or information provided by the invention would enable the robot to properly characterize the object so that decisions could be made about grasping, moving, manipulating, placing, releasing or otherwise handling the object.

Particularly with respect to normal loading, the system 11 is capable of providing high contrast or well defined characterization of an object in contacts, high resolution of the magnitude of the normal load produced by such contact and at least moderate resolution of the shape or contour of the object. This is due primarily to the fact that normal loads imposed by an object contacting the touch surface 17 create a deflection of only those individual sensitive sites 19 located immediately beneath the object, and this deflection or mechanical response is sensed by separate transducer means associated with each affected sensitive site 19. Due to the presence of plates 12 and 13 and the compartmentalized construction of the sensitive sites 19, normal loads applied by an object to the touch surface 17 cause little or no detectable deflection in sensitive sites 19 which are not directly under load. In addition to this mechanical isolation of adjacent sensitive sites 19, the provision of each sensitive site 19 with separate transducer means effectively isolates the electronic aspect of the transduction means herein preventing cross-talk and avoiding the need for complex pattern recognition systems. As a result, the configuration of this invention has been found to provide much better contrast than prior art tactile sensors in which a continuous touch surface is electrically responsive to contact with an object.

Other advantages are inherent in the construction of the sensitive sites 19 of touch surface 17 which adds to the versatility of system 11. In the figures, the sensitive sites 19 are shown having a frusto-conical shaped raised section 20 with an annular hollow section 22 between the pin structure 21 and openings 15 in plates 12 and 13.

Two factors affect the amount of deflection which a sensitive site 19 undergoes under the application of a given load. These factors are the geometrical configuration of the sensitive site 19 and the type of material used to fabricate such site 19. Considered together, these factors determine the compliance of the sensitive site 19. The compliance of a sensitive site may be altered, then, by changing the geometry of the sensitive site and/or using an elastomeric material or lower or higher modulus of elasticity.

The capability of altering the compliance of the sensitive sites 19 is a valuable advantage of this invention over prior art devices because it allows the deflection and force sensitivity requirements of different applications to be accommodated equally well with a single system 11.

For example, assume that the system 11 is to be utilized in a gripper hand for an industrial robot. Also assume that a heavy object is to be manipulated which will initially require a large grasping force to lift, and then recognition of the surface of the object is needed for proper handling and placement. In this application, the system 11 would preferably provide relatively low sensitivity or resolution up to the force required to lift the object, but high sensitivity at higher loads so that the contours of the object could be detected.

To accommodate this requirement, the geometry of the sensitive site 19 or the modulus of the material used to fabricate it could be altered to produce minimal deflection of the pin structure 21, for example, up to the load imposed by the weight of the object, and the increased deflection in the pin structure 21 for forces of higher magnitude. As discussed above, the transducer means herein sense the deflection of the pin structure 21 and produce a signal directly proportional to such deflection. Minimum downward movement of the pin structure 21 would produce a correspondingly minimal change in the signal produced by the transducer means. In the example above, the system 11 would thus provide low sensitivity in response to such minimal movements of the pin structure 21. However, as the pin structure 21 moves downwardly to a greater extent due to the increased load applied beyond the weight of the object, a correspondingly higher change in the signal is produced by the transducer means. Thus, the system 11 provides high sensitivity at such higher loads.

In another instance, it may be desirable to provide system 11 with a high sensitivity of resolution under relatively small loading conditions, and then lesser sensitivity under lighter loads. The manipulation and characterization of lightweight objects or lightweight and heavyweight objects by a single device could fall into this category. The geometry of a sensitive site 19 could be altered by reducing the thickness of the elastomer in the raised section 20 so that rapid downward deflection of pin structure 21 would occur under relatively small loads until the raised section 20 snubbed against the top plate 12, at which time minimal further deflection would occur. The transducer means would thus detect a relatively large change in deflection of pin structure 21 under small loads and produce a proportional change in their signal transmitted to the electronic circuitry. The system 11 would thus achieve high sensitivity under such loading conditions. However, once the raised section 20 snubbed out, only minimal deflection of pin structure 21 would occur and the sensitivity of the system 11 would be relatively low.

The various geometrical and material variations, or combinations of the two, in forming the sensitive sites 19 provide a wide range of options in obtaining a linear or various non-linear responses to the deflection of the pin structure 21 caused by contact of an object with the touch surface of the tactile sensing system 11. The sensitivity to the magnitude of normal loads applied to the system 11 may thus be altered, as desired, to accommodate the requirements of a variety of applications.

In some instances, it may be desirable to detect shear forces applied by an object to the touch surface 11. For example, a robot arm may be required to grasp an object, recognize its configuration and then manipulate the object in some manner such as by twisting or turning it prior to release. While the detection of the normal forces will still be required for such an application to determine the presence, size and shape of the object, the shear forces developed between the object and the touch surface 17 of the system must be determined to detect incipient slip and slip as the object is being clamped, lifted and then manipulated.

Another feature of the construction of sensitive sites 19 should be noted in connection with the application of shear forces to the touch surface 17. As shown in the figures, the pin structure of each sensitive site 19 is elongated and extends downwardly through the openings 15 formed in plates 12 and 13. The relatively close fit between the pin structures and opening 15 has the effect of essentially eliminating any cocking motion of the base of the pin structures which could otherwise occur due to lateral components of shear forces applied to the touch surface 17. Such cocking motion, if not eliminated, could adversely affect the accuracy of measurements of the pin structure deflection taken by the various transducer means disclosed herein. Therefore, the means for detection of normal and shear loads is effectively decoupled with the construction of sensitive sites 19 in accordance with this invention.

Referring now to FIGS. 2 and 6a-b, one embodiment of the shear load detection transducer means of the system 11 is shown. A pair of brackets 71 are mounted at either end of the base section 23 and extend upwardly toward the plate 13. A flange 73 is formed at the upper end of each bracket 71 which extends inwardly between a photo emitter 75 mounted on the lower surface of plate 13 near the middle and an array of photo detectors are mounted on the upper surface of the transducer platform 27 below the photo emitter 75. As shown in FIG. 6, there are four photo detectors, 79a, b, c and d, disposed at equal intervals apart. Although four photo detectors are shown, it should be understood that as little as two detectors or more could be utilized to accomplish the shear detection concept described herein. A window 81 is formed in each of the flanges 73 to permit light from the emitter 75 to be sensed by the detectors 79a-d.

In the undeflected position, essentially all of the light produced by the emitters 75 passes through the window 81 in flanges 73, and is sensed by the detectors 79a-d. Assuming a shear load $S_1$ is applied to the touch surface 17 as shown in FIG. 6a, the plate 13 and transducer platform 27 will move together causing detector 79c to be at least partially covered. The reduction in the intensity of light sensed by the detector 79c will be directly proportional to the magnitude of $S_1$. Similarly, under the application of a shear load $S_2$ to the touch surface 17, detector 79b will be at least partially covered with the light intensity it senses being directly proportional to the magnitude of $S_2$. Shear loads applied at oblique angles to the direction of shear forces $S_1$ and $S_2$ within the plane of plate 13 will create different magnitudes of light intensity which can be detected both as to magnitude and direction by the detectors 79a-d and processed by the electronic circuitry described below.

Figures 7, 7A, 7B, 8, 8A, 9, 9A:
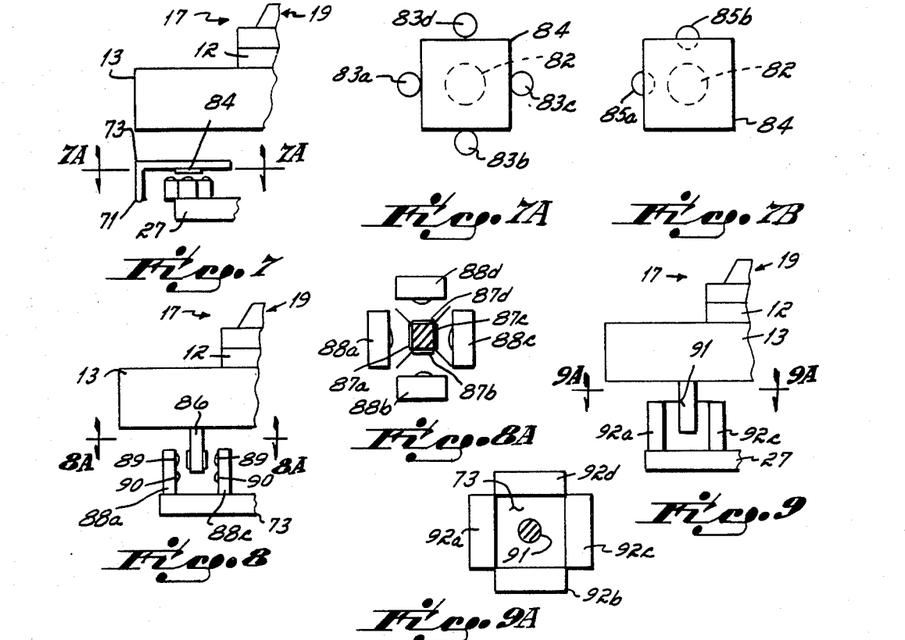
FIG. 7 is a view in partial cross-section of another embodiment of the shear detection transducer means herein.
FIG. 7a is a view of one form of the shear detection transducer means of FIG. 7 taken generally along line 7a—7a of thereof.
FIG. 7b is a view of another form of the FIG. 7 shear detection transducer means taken along line 7a—7a of FIG. 7.
FIG. 8 is a view in partial cross-section of a further embodiment of the shear detection transducer means.
FIG. 8a is a view of the shear detection transducer means of FIG. 8 taken generally along line 8a—8a thereof.
FIG. 9 is a still further embodiment of the shear detection transducer means of the invention.
FIG. 9a is a partial view of the FIG. 9 embodiment, taken generally along the line 9a—9a in FIG. 9.

Further embodiments of the transducer means for detecting the magnitude and location of shear forces applied to the touch surface 17 are shown in FIGS. 7-9a. Referring now to FIGS. 7-7b, a reflected-light shear detection means is illustrated. In FIG. 7a, a single emitter 82 is surrounded by four equally spaced detectors 83a-d which are all mounted at either end of the top surface of transducer platform 27. Only one of the emitter-detector groups is shown in the drawings. Mounted to the flange 73 of bracket 71 immediately above the emitter 82 is a reflective surface 84. Movement of the transducer platform 27 with the touch surface 17 in response to a shear force causes different ones of the detectors 83a-d to receive more or less reflected light back from the surface 84. Such changes in the amount of light received causes proportionately changed signals to be transmitted to the electronic circuitry herein. FIG. 7b is a variation of FIG. 7a wherein two detectors 85a,b are utilized to measure changes in the amount of light reflected back from surface 84.

A further variation of reflected light shear force transducer means is shown in FIGS. 8 and 8a. In this embodiment, a four-sided pin 86 having reflective surfaces 87a-d on each side is mounted to the bottom surface on either side of plate 13. Only one pin 86 is shown in the figures. Four blocks 88a-d, each having an emitter 89 and detector 90 mounted thereto one over the other, are disposed directly across from respective reflective surfaces 87a-d of pin 86. The blocks 88a-d are mounted at their lower end in the flange 73 of bracket 71. As can be appreciated from viewing FIG. 8c, lateral movement of the pin 86 with plate 13 in any direction will cause more or less light to be reflected from the emitter 89 to the detector 90 on respective blocks 88a-d. The change in light intensity sensed by any of the detectors 90 causes a proportionately changed signal to be transmitted from the detectors 90 to the electronic circuitry herein.

Another shear force transducer means is shown in FIGS. 9, 9a, wherein a magnetized pin 91 extends downwardly from the underside of plate 13 on each end thereof. Again, only one end of plate 13 is shown in the figures. Four Hall effect transducers 92a-d are mounted at intervals to the upper surface of the flange 73 and extend upwardly about pin 91. Thus, movement of pin 91 with plate 13 in response to a shear force causes one or more of the Hall effect transducers 91 to sense a changed magnetic field intensity. A signal proportional to such change is then transmitted by the respective Hall effect transducers to the circuitry for processing as described below.

Figure 10:
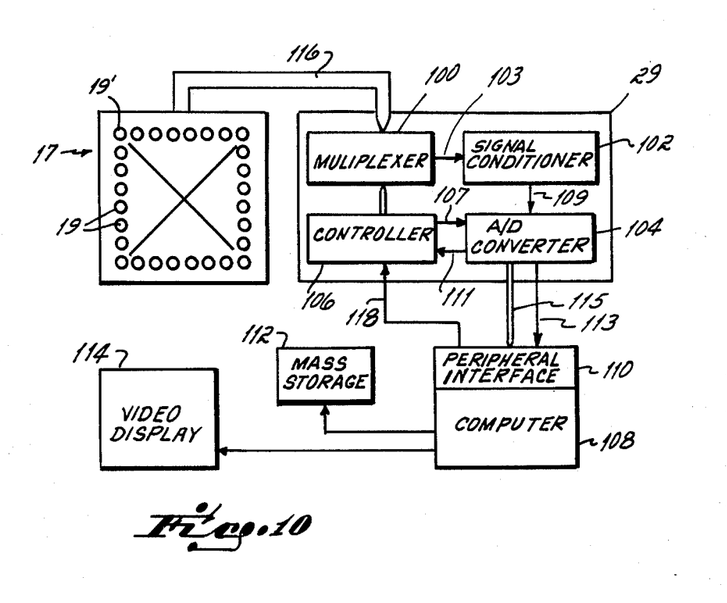
FIG. 10 is a schematic view of the localized and remote data processing means herein.

Referring now to FIG. 11, a schematic diagram of the electronic circuitry used in the tactile sensing system 11 of this invention is shown. As mentioned above, the circuitry herein consists of components mounted to the electronics platform 29 which has been identified as local circuitry, and external circuitry consisting of a computer, a buffer or peripheral interface and display means. The configuration and operation of the circuitry described below is not intended to be restrictive, and many modifications or substitutions could be made to satisfy the signal processing requirements of the system 11.

The components mounted on the electronics platform 29 include a standard multiplexer 100, a signal conditioner 102, an analog to digital (A/D) convertor 104 and a controller 106. The external circuitry includes a computer 108, a peripheral interface 110 which electrically connects the computer 108 to the components on the electronics platform 29, mass storage 112 and a video display 114.

The electronics operate as follows. Each of the transducer means associated with the sensitive sites 19 produce a continuous signal, first in the form of a current and then after being dropped through resistors in the form of an analog voltage in the range of 0–1 volts. In the embodiment of system 11 shown in the drawings, there are sixty-four sensitive sites 19, so sixty-four signals, in parallel, are transmitted by an analog data line 116 to the multiplexer 100. The components on the electronics platform 29 function to convert each of the sixty-four analog signals into digital format for introduction into the computer 108.

The analog-to-digital conversion is accomplished as follows. A data strobe is transmitted from the computer 108 to the controller 106 through a data stobe line 118. The data strobe commands the controller 106 to provide an address to the multiplexer 100, which then scans each of the sixty-four signals from the sensitive sites 19 in serial fashion. For example, the signals from the sensitive sites 19 may be scanned beginning with the site 19' and moving left-to-right, top-to-bottom until all sites 19 are scanned.

The multiplexer 100 recognizes the address from the controller 106 as an instruction to scan the sixty-four signals in a manner such as suggested above, and to switch each analog signal scanned to the signal conditioner 102 through switching signal line 103. The signal conditioner 102 amplifies the signals to a voltage in the range of 1–10 volts from 0–1 volts, and presents the amplified signal to the A/D convertor 104.

Each of the sixty-four signals from the sensitive sites is scanned as a result of a separate address sent to the multiplexer 100 from the controller 106. The controller 106 allows for the delay associated with the scanning operation and the amplification of the signal in the signal conditioner 102, so that at the time the amplified signal is presented to the A/D convertor 104, a start convert signal is sent by the controller 106 through the start convert line 107 to the A/D convertor 104. This signal instructs the A/D convertor to accept the amplified signal from the signal conditioner 102 through an amplified signal line 109, and convert it to digital format. Once the conversion is complete, the A/D convertor 104 provides a conversion complete signal through convert complete line 111 to the controller 106. The controller 106 then instructs the multiplexer 100 to scan the next signal, and the process is repeated for each of the sixty-four signals.

After converting an analog signal to digital format, which can be read by the computer 108, the A/D convertor 104 provides a data ready signal to the computer 108 through a data ready line 113. The computer 108 accepts the digital signal through digital data line 115. When all of the analog signals from the sensitive sites 19 have been serially selected, converted to digital form and transmitted to the computer 108, the controller 106 resets and waits for the next data probe.

After reading the digital data on each data ready signal, the computer 108 is operable to process such data in a variety of forms depending on the requirements of an application. The computer 108 may be programmed using well known techniques to process the data and display it on a video display 114 or store such data in mass storage 112 for future reference and use. Programs have been written, for example, to display the data in numerical, grid format on a video display 114 with a number corresponding to the magnitude of the signal from each sensitive site 19 being displayed on an 8×8 grid. Many other display formats are possible.

The foregoing discussion has indicated the manner in which signals produced by the transducer means associated with sensitive sites 19 are processed by the electronic circuitry herein. With respect to signals produced by the shear detection transducer means such as in FIGS. 6–9a, the processing is essentially the same with some variation particularly in the program for computer 108.

Each signal produced by the detectors associated with the shear detection transducers herein is transmitted in parallel to the multiplexer 100, and the operation for converting such signals from analog to digital format is conducted. The digital signals are presented to the computer 108 serially, so that the computer 108 can identify which signal comes from each detector. A summation of the signals produced by the shear detection transducers on each side of touch surface 17 would provide an output representing the translation of the touch surface 17 relative to the base section 23. The difference of the signals produced by the shear detection transducers on each side of touch surface 17 would provide an output representing the rotation of the touch surface 17 relative to the base 23. Knowing the distance between the shear detection transducers, programs may be written for computer 108 to use the outputs, calculated by computer 108, representing the translation and rotation of the touch surface 17 to determine the magnitude, location, and direction of shear forces applied to touch surface 17 with at least moderate resolution.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A device for detecting, discriminating and identifying a number of mechanical contact parameters when contacting an object including presence, pressure, pressure pattern, topography, slip, incipient slip and the like comprising:

a touch surface for contacting said object, said touch surface being movable in a horizontal plane;
a plurality of sensitive sites disposed in an array on said touch surface, said sensitive sites being deflected in response to a normal force applied by contact with said object, said touch surface being moved laterally in said horizontal plane in response to a shear force applied by contact with said object;

normal force detection transducer means associated with each of said sensitive sites, said normal force transducer means being operable to sense said deflection of said sensitive sites and produce an electrical signal proportional to the magnitude of said deflection;

shear force detection transducer means associated with said touch surface, said shear force transducer means being operable to sense said lateral motion of said touch surface and produce an electrical signal proportional to said lateral motion;

signal processing means operable to receive said electrical signals from said normal force and shear force transducer means and provide information identifying said contact parameters of said object.

2. The device of claim 1 wherein said shear force transducer means are Hall effect transducers.

3. The device of claim 1 wherein said normal force detection transducer means associated with each said sensitive sites comprises magnetic means capable of producing a magnetic field and electromagnetic sensing means operable to sense the intensity of said magnetic field produced by said magnetic means, said electromagnetic sensing means being adapted to be disposed relative to said magnetic means and said sensitive sites so that deflection of said sensitive sites from an undeflected position in response to a normal load causes a proportional change in the proximity and therefore intensity of said magnetic field sensed by said electromagnetic sensing means, said electromagnetic sensing means being operable to produce an electrical signal directly proportional to said change in intensity of said magnetic field.

4. The device of claim 1 wherein said shear force detection transducer means associated with said touch surface comprises magnetic means capable of producing a magnetic field and electromagnetic sensing means operable to sense the intensity of said magnetic field produced by said magnetic means, said electromagnetic sensing means being adapted to be disposed relative to said magnetic means and said touch surface so that lateral movement of said touch surface in response to a shear load causes a proportional change in the proximity and therefore intensity of said magnetic field sensed by said electromagnetic sensing means, said electromagnetic sensing means being operable to produce an electrical signal proportional to said change in intensity of said magnetic field.

5. The device of claim 4 which further includes a fixed support means disposed below said touch surface, said touch surface being laterally movable relative to said fixed support means, said magnetic means of said shear force detecting transducer means being adapted to be mounted to one of said touch surface or said fixed support means, said electromagnetic sensing means of said shear force detecting transducer means being adapted to be mounted to the other of said touch surface and said fixed support means and adjacent said magnetic means, whereby upon application of a shear load to said touch surface said magnetic means and said electromagnetic sensing means move laterally relative to one another so that the proximity and therefore intensity of said magnetic field produced by said magnetic means and sensed by said electromagnetic sensing means changes in proportion to said lateral movement of said touch surface.

6. The device of claim 1 wherein said normal force detection transducer means associated with each said sensitive sites comprises light reflecting means, photoemitter means operable to direct a light beam to said light reflecting means, and photodetector means operable to receive light reflected by said light reflecting means from said photoemitter means, said photoemitter means and said photodetector means being adapted to be disposed relative to said light reflecting means and said sensitive sites so that deflection of said sensitive sites in response to a normal load causes a proportional change in the intensity of light reflected to said photodetector means by said light reflecting means from said photoemitter means, said photodetector means being operable to produce an electrical signal proportional to said change in intensity of light received from said photoemitter means.

7. The device of claim 1 wherein said shear force detection transducer means associated with said touch surface comprises light reflecting means, photoemitter means operable to direct a light beam to said light reflecting means, and photodetector means operable to receive light reflected by said light reflecting means from said photoemitter means, said photoemitter means and said photodetector means being adapted to be disposed relative to said light reflecting means and said touch surface so that lateral movement of said touch surface in response to shear load applied thereto causes a proportional change in the intensity of light reflected by said light reflecting means to said photodetector means from said photoemitter means, said photodetector means being operable to produce an electrical signal proportional to said change in the intensity of light received from said photoemitter means.

8. The device of claim 7 which further includes a platform secured to said touch surface so as to be laterally movable therewith, a fixed support means disposed between said platform and said touch surface, said light reflecting means being mounted to one of said platform and said fixed support means, said photoemitter means and photodetector means being mounted to the other of said platform and said fixed support means in alignment with said light reflecting means, whereby upon application of a shear load to said touch surface said light reflecting means and said photodetector means and photoemitter means move laterally relative to one another so that the intensity of light reflected by said light reflecting means to said photodetector means from said photoemitter means changes in proportion to said lateral movement of said touch surfaces.

9. The device of claim 8 wherein said photoemitter means is a single photoemitter and said photodetector means is a plurality of individual photodetectors disposed at equal intervals about said photoemitter, whereby upon application of a shear load to said touch surface said photoemitter and said photodetectors move laterally relative to said light reflecting means so that the intensity of light reflected to said photodetectors by said light reflecting means from said photoemitter changes in proportion to the extent and direction of said lateral movement of said touch surface.

10. The device of claim 7 which further includes a fixed support disclosed below said touch surface, a pin having four sides each formed with a light reflecting surface, said pin being adapted to be mounted to one of said touch surface and said fixed support, four block means each disposed in alignment with a respective one of said sides of said pin and being adapted to be mounted on the other of said touch surface and fixed support, each of said four block means having a photoemitter and a photodetector mounted thereto, said photoemitter of each of said block means being operable to direct a light beam to the light reflecting surface of a respective side of said pin facing said block means and the associated photodetector of said block means being operable to receive light reflected by said respective light reflecting surface, whereby upon application of a shear load to said touch surface said pin and said block means move laterally relative to one another so that the intensity of light reflected by said light reflecting surfaces of said pin and received by respective photodetector means of said block means changes in proportion to the extent and direction of said lateral movement of said touch surface.

11. A device for detecting, discriminating and identifying mechanical contact parameters when contacting an object, comprising:
 a generally horizontally extending touch surface for contacting said object, said touch surface being mounted for substantially translational horizontal movement in response to a shear force applied by contact with an object;
 transducer means for sensing said movement of said touch surface and for producing an electrical signal proportional to said movement; and
 signal processing means for receiving electrical signals from said transducer means and for identifying the magnitude and direction of said shear force applied to said touch surface by contact with said object.

12. A tactile sensing system for detecting, discriminating and identifying a number of mechanical contact phenomena when contacting an object including presence, pressure, topography and the like comprising:
 a base section;
 plate means formed with a plurality of openings in an array, said plate means being disposed above said base section and mounted for lateral movement relative thereto by resilient connectors;
 a unitary touch surface overlying and affixed to said plate means and having a plurality of sensitive sites in an array corresponding to said array of said openings in said plate means, each of said sensitive sites including a raised section extending upwardly from said touch surface for contact with said object and a pin structure integrally connected with said raised section and extending downwardly through an underlying one of said openings in said plate means, said sensitive sites being flexible enabling said pin structures to deflect vertically downwardly in response to a normal force applied by contact of said object with said sensitive sites;
 a lower platform disposed adjacent said base section and an upper platform disposed between said lower platform and said plate means, said upper and lower platforms being connected together and to said plate means for unitary movement;
 a plurality of transducer means mounted in said array on said upper platform, one of said transducer means being disposed adjacent said downwardly extending pin structure of each of said sensitive sites, said transducer means being operable to sense the magnitude of said deflection of said pin structures under the application of a normal force imposed by contact with said object and to produce a signal proportional to said magnitude of deflection;
 local data processing means mounted on said lower platform, said local data processing means receiving said electrical signals produced by said transducer means, said local data processing means being operable to convert said electrical signal from each of said transducer means from analog to digital format in serial fashion; and
 remote data processing means electrically connected to said local data processing means, said remote data processing means being operable to receive and process said digital signals from said local data processing means to provide information identifying said contact parameters of said object.

13. A tactile sensing system for detecting, discriminating and identifying a number of mechanical contact phenomena when contacting an object including presence, pressure, pressure pattern, topography, slip, incipient slip and the like comprising:
 a base section;
 plate means formed with a plurality of openings in an array, said plate means being disposed above said base section and mounted for lateral movement relative thereto by resilient connectors;
 a unitary touch surface formed overlying and affixed to said plate means and having a plurality of sensitive sites in an array corresponding to said array of said openings in said plate means, each of said sensitive sites including a raised section extending upwardly from said touch surface for contact with said object and a pin structure integrally connected with said raised section, said pin structures extending downwardly through said openings in said plate means, said sensitive sites being flexible enabling said pin structures to deflect vertically downwardly in response to a normal force applied by contact of said object with said sensitive sites, said touch surface and said plate means being laterally moveable in response to shear force exerted on said touch surface by contact with said object;
 a lower platform disposed adjacent said base section and an upper platform disposed between said lower platform and said plate means, said upper and lower platforms being connected together and to said plate means for unitary movement;
 a plurality of normal force sensing transducer means mounted in said array on said upper platform, one of said transducer means being disposed adjacent said downwardly extending pin structure of each of said sensitive sites, said transducer means being operable to sense the magnitude of said deflection of said pin structures under the application of a normal force imposed by contact with said object and to produce a signal proportional to said magnitude of deflection;
 shear detection transducer means for sensing said lateral movement of said touch surface in response to the application of a shear force thereto by contact with said object, said shear detection transducer means producing an electrical signal proportional to said lateral movement of said touch surface;
 local data processing means mounted on said lower platform, said local data processing means receiving said electrical signals from said normal force sensing transducer means and said shear detection transducer means and being operable to convert said electrical signals from each of said transducer means from analog to digital format in serial fashion; and remote data processing means electrically connected to said local data processing means, said remote data processing means being operable to receive and process said digital signals from said local data processing means to provide information identifying said contact parameters of said object.

14. A device for sensing contact parameters of an object, comprising:
a touch surface for contacting said object;
mounting means mounting said touch surface for substantially translational lateral movement in response to a shear force imposed thereon by contact with said object;
a plurality of sensitive sites disposed in an array on said touch surface, said sensitive sites undergoing a mechanical response to a normal force imposed thereon by contact with said object;
transducer means associated with each said sensitive sites, said transducer means including magnetic means capable of producing a magnetic field and electromagnetic sensing means operable to sense the intensity of said magnetic field produced by said magnetic means, said electromagnetic sensing means being adapted to be disposed relative to said magnetic means so that said mechanical response of said sensitive sites upon contact with an object causes a proportional change in the proximity and therefore intensity of said magnetic field sensed by said electromagnetic sensing means, said electromagnetic sensing means being operable to produce an electrical signal proportional to said change in intensity of said magnetic field; and
signal processing means operable to receive said electrical signals from said electromagnetic sensing means of said transducer means and provide information identifying said contact parameters of said object.

15. The device of claim 14 wherein said transducer means includes a pin adapted to be deflected by at least one of said sensitive sites, said pin having a magnetized portion, said pin being disposed relative to said electromagnetic sensing means such that said magnetic field produced by said magnetized portion is sensed by said electromagnetic sensing means, said pin being adapted to be deflected by at least one of said sensitive sites in response to contact of an object with said sensitive sites to move said magnetized portion toward said electromagnetic sensing means so that a magnetic field of an intensity proportional to the deflection of said pin is sensed by said electromagnetic sensing means.

16. A device for sensing contact parameters of an object comprising:
a touch surface for contacting said object;
mounting means mounting said touch surface for substantially translational lateral movement in response to a shear force imposed thereon by contact with said object;
a plurality of sensitive sites disposed in an array on said touch surface, said sensitive sites undergoing a mechanical response to a normal force imposed thereon by contact with said object;
transducer means associated with each said sensitive sites including light reflecting means, photoemitter means operable to direct a light beam to said light reflecting means, and photodetector means operable to receive light reflected by said light reflecting means from said photoemitter means, said photoemitter means and said photodetector means being adapted to be disposed relative to said light reflecting means and said sensitive sites so that said mechanical response of said sensitive sites upon contact with an object causes a proportional change in the intensity of light reflected to said photodetector means by said light reflecting means from said photoemitter means, said photodetector means being operable to produce an electrical signal proportional to said change in intensity of light received from said photoemitter means; and
signal processing means operable to receive said electrical signals from said photodetector means of said transducer means and provide information identifying said contact parameters of said object.

17. The device of claim 16 wherein said transducer means includes a pin adapted to be deflected by at least one of said sensitive sites, said pin having a light reflecting surface facing said light beam from said photoemitter means, said pin being disposed relative to said photoemitter means and photodetector means such that light is reflected by said light reflecting surface of said pin from said photoemitter means to said photodetector means, said pin being adapted to be deflected with at least one of said sensitive sites in response to contact of an object with said sensitive site so that light of an intensity proportional to the deflection of said sensitive site is reflected by said light reflecting surface of said pin from said photoemitter means to said photodetector means.

18. A tactile sensor device for sensing contact parameters of objects, comprising:
a touch responsive member having an array of sensitive sites on an outer surface thereof, said surface of said member being engageable with said objects, and said sites being deflectable inwardly substantially independently of each other in response to the imposition thereon of normal forces produced by said engagement;
a base member;
mounting means mounting said touch responsive member for substantially translational movement thereof generally parallel to the plane of said surface thereof in response to the imposition thereon of shear forces produced by said engagement;
transducer means for sensing, and for producing data signals representative of, said deflection of said sites.

19. A device as in claim 18, and further including transducer means for sensing, and for producing data signals representative of, said lateral translatory movement of said touch responsive member.

20. A device as in claim 18, wherein said mounting means mounts said member for directionally universal movement generally parallel to said surface thereof.

21. A device as in claim 18, wherein said touch responsive member is formed of resilient and durable elastomeric material.

* * * * *